(12) United States Patent
Zuendorf et al.

(10) Patent No.: US 7,599,468 B2
(45) Date of Patent: Oct. 6, 2009

(54) BONE DENSITY CALIBRATION METHOD AND SYSTEM

(75) Inventors: Gerhard Zuendorf, Bonn (DE); Lutz Ritter, Bornheim (DE); Martin Schroeder, Luebeck (DE)

(73) Assignee: Sicat GmbH & Co. KG, Bonn (DE)

( * ) Notice: Subject to any disclaimer, the term of this patent is extended or adjusted under 35 U.S.C. 154(b) by 0 days.

(21) Appl. No.: 11/913,457

(22) PCT Filed: Apr. 28, 2006

(86) PCT No.: PCT/EP2006/003982

§ 371 (c)(1),
(2), (4) Date: Nov. 2, 2007

(87) PCT Pub. No.: WO2006/117147

PCT Pub. Date: Nov. 9, 2006

(65) Prior Publication Data

US 2008/0253506 A1     Oct. 16, 2008

(30) Foreign Application Priority Data

May 4, 2005    (DE) .................. 10 2005 021 327

(51) Int. Cl.
*A61B 6/14* (2006.01)
(52) U.S. Cl. .............................. 378/38; 378/39
(58) Field of Classification Search ............ 378/18, 378/38–40, 53–56, 62, 204, 207, 901
See application file for complete search history.

(56) References Cited

U.S. PATENT DOCUMENTS

| | | | |
|---|---|---|---|
| 5,335,260 A * | 8/1994 | Arnold | 378/207 |
| 6,190,042 B1 | 2/2001 | Dove et al. | |
| 6,377,653 B1 * | 4/2002 | Lee et al. | 378/54 |
| 6,674,834 B1 | 1/2004 | Acharya et al. | |
| 6,904,123 B2 * | 6/2005 | Lang | 378/54 |
| 7,050,534 B2 * | 5/2006 | Lang | 378/54 |
| 7,058,159 B2 * | 6/2006 | Lang et al. | 378/54 |
| 7,292,674 B2 | 11/2007 | Lang | |
| 2002/0150205 A1 | 10/2002 | Adriaansz | |
| 2003/0235265 A1 | 12/2003 | Clinthorne et al. | |
| 2007/0058786 A1 * | 3/2007 | Michael | 378/207 |

FOREIGN PATENT DOCUMENTS

WO       WO 03071934 A      9/2003

* cited by examiner

*Primary Examiner*—Courtney Thomas
(74) *Attorney, Agent, or Firm*—Millen, White, Zelano & Branigan, P.C.

(57) ABSTRACT

Disclosed is a method for pictorially representing and determining tissue densities of a body region, especially in the mouth/jaw/face region (1), of a patient. According to said method, a set of three-dimensional image data representing the body region as well as calibration data that is provided as three-dimensional image data and represents a calibration phantom (5, 8, 15) having a previously known density are photographed by generating an image while the tissue densities are derived from a comparison of the calibration data with the image data. The image data and the calibration data are photographed in the framework of the same shot and in an upright position of the patient, particularly during sitting or standing. The calibration phantom (5, 8, 15) is held in the immediate vicinity of the body region (1) that is to be photographed during the shot by means of a fixture (4, 10, 14) which is fixed independently of the patient's body and in a defined relation to the imaging device.

20 Claims, 2 Drawing Sheets

BONE DENSITY CALIBRATION METHOD AND SYSTEM

Figure 1:
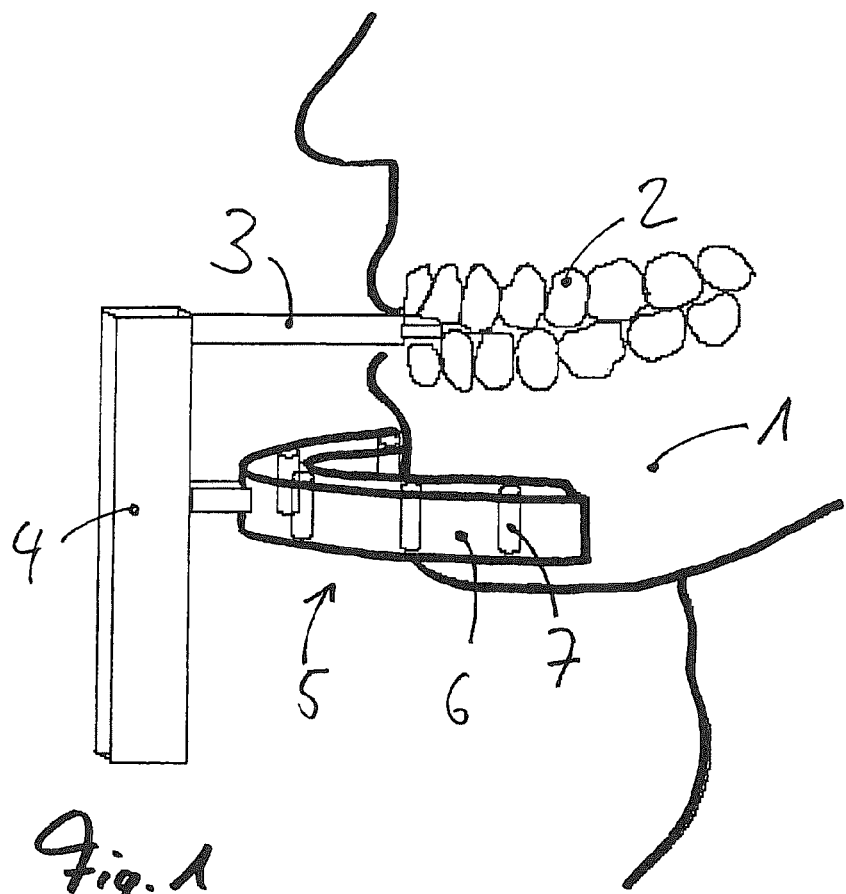

The present invention relates to a method for pictorially representing and determining tissue densities of a body region, especially in the jaw region, of a patient, wherein a set of three-dimensional image data representing the body region as well as calibration data that is provided as three-dimensional image data and represents a calibration phantom having a previously known density are photographed by generating an image, wherein tissue densities are derived from a comparison of the calibration data with the image data. The invention also relates to a system to implement such a method.

Generally speaking, such spatially resolved determination of bone density is, in particular, of great interest in dental implantology, because said determination contributes to the avoidance of errors when planning tooth implants. Planning of an implant is often undertaken on the basis of three-dimensional representation of a human mouth/jaw/face region (hereinafter simply referred to as the "jaw region"), wherein the representation is based on data which, for example, have been generated by means of computer volume tomography (DVT) or by means of computer tomography (CT). In such representations the voxel values, i.e. the colour values of the individual volume elements, correspond to the different material characteristics of the scanned volume.

However, as is well known, these values are initially present only as relative values; they can be converted to absolute values only by means of calibration data. Thus, calibration of image data in the case of CT takes place in Hounsfield units. However, the use of Hounsfield units in the case of bone density determination is associated with severe disadvantages in that Hounsfield units are influenced by a host of factors. For example, Hounsfield units depend both on the effective energy of X-ray radiation and on scattered radiation, and thus on the shape of the body part to be examined. This results in an image of the same object by two different devices returning different Hounsfield values.

In order to be able to make definite inferences about bone density distribution, phantoms made of bone-equivalent material of known density have been used for calibration in units of bone density. In the case of CT, such a method is known (K. Maki et al., Dentomaxillofacial Radiology, (1997) 26, 39-44), where during imaging a U-shaped calibration phantom is placed on the jaw of the patient who is lying down. However, due to the calibration phantom that is awkward to handle and that can hardly be used in a reproducible manner, in practical applications the method described therein is suitable only to a limited extent.

From US 2002/0114425 A1, a method for determining the structure and density of jawbones in the context of conventional X-ray projection imaging is known. In order to obtain meaningful results in this method, the calibration phantom, for example by affixation to a tooth, is arranged such that it rests directly in front of the X-ray film to be exposed, so that there is no further absorbent material present between the phantom and the film. Finally, as far as the reliability of results determined according to this method are concerned, it is essential that the projection of the calibration phantom as an external standard [GZ1] is not overlaid by other absorbent structures, for example bones. In this method, too, which is only suitable for two-dimensional imaging, the calibration phantom is awkward to handle, wherein the arrangement of the phantom in later imaging is also not reproducible.

It is the object of the invention to create a method and a system that with simple means can be implemented in an economical manner and that, with simple handling that is suitable for practical application, make possible three-dimensional density determination of the tissue in the jaw region, in particular of the jawbone, with good accuracy and reproducibility. Moreover, it is the object of the invention to state the simplest possible type of fixture for a calibration phantom.

These objects are met with the method according to claim 1 and with the system according to claim 7. Advantageous embodiments of the invention are mentioned in the respective subordinate claims.

An essential core idea of the method according to the invention first consists of making possible three-dimensional imaging containing the jaw and the calibration phantom in an upright position of the patient, i.e. in particular with the patient sitting or standing. In this position patient handling is easier and there is no need for special movable supports, which represent considerable design expenditure and financial expenditure in an imaging system. The upright positioning, according to the invention, during imaging thus allows significantly more compact and thus user-friendly imaging systems. Furthermore, the use of a jig to fix the patient becomes possible, which results in a further reduction in movement artefacts.

There is a certain advantage when compared to positioning with the patient lying down, in that in the upright position the anatomy of the patient is in its "natural" relaxed state, in which there is a reduced danger of displacement of the bones relative to each other as a result of one-sided loads, which displacement would influence subsequent planning. This advantage is particularly significant when imaging the jawbones that are displaceable relative to each other.

As mentioned, a significant further aspect consists of incorporating the calibration phantom directly in the three-dimensional image, wherein the calibration phantom is not held in or on the body of the patient, but instead on a stand in the immediate vicinity of the region to be imaged. In this context the term "in the immediate vicinity" refers to a situation where the calibration phantom and the skull can be imaged together in a single scan. In an ideal case the calibration phantom is situated at most a few centimeters from the region of interest; in the case of imaging the jaw, said calibration phantom is, in particular, also held in the oral cavity. In this arrangement in any case the phantom is fixed in a defined relation to the imaging device, advantageously also in a defined relation to the patient, for example by way of the jig, so that particularly good reproducibility of the images is ensured.

From a comparison with the data obtained from the calibration phantom of known density, the absolute density value of the tissue can be inferred. The method according to the invention also provides a special advantage in that it makes it possible to obtain images within a three-dimensional volume that contains both the body region and the calibration phantom, which images are free of any overlay. Accurate determination, for example, of the bone densities can only be ensured as a result of error-free imaging.

The invention is associated with another significant advantage in that it contributes to reproducible positioning of the patient in relation to the imaging system, which is advantageous in the evaluation of image data, and which even makes it possible to repeat individual images. Thus, according to the invention, a convenient solution for precise and easy positioning of the calibration phantom relative to the patient during imaging is created, with the patient sitting or standing. The invention makes it possible to create dental volume tomography images, in particular cone-beam CT images, which provide direct bone density calibration by means of calibration phantoms.

In order to simplify subsequent uniform evaluation and in order to make possible direct comparison between the image data obtained from the patient and from the phantom, even in the case of the phantom being arranged outside the patient, the image data and the calibration data are stored in the same data record, which thus represents a three-dimensional image of the jaw region and of the associated calibration phantom.

According to the invention, for the purpose of bone density determination the method known as quantitative CT (QCT) is used, which method is in particular advantageous in the case of three-dimensional imaging, and which method is based on calibration of the system using the calibration phantom. Advantageously, the calibration phantom comprises bone-equivalent material of known density, for example hydroxyapatite embedded in water-equivalent material. Such a phantom, with imaging of the patient and the phantom at the same time, and with a comparison of the grey values of the bone and of the phantom, allows reliable inference relating to the absolute values of the bone density in the scanned bone at high resolution. The accuracy of the density determination improves the closer the calibration phantom is placed to the jaw. The invention makes it possible to better take into account error sources which are, for example, caused by beam hardening or by the individual geometry of the body to be scanned, and which error sources differ from location to location.

In the simplest case the actual bone density determination can take place by the "image", i.e. the processed data record of the jaw and the associated phantom, which data record has been presented as an image, being inspected by the viewer, in particular by the therapist. This image shows the structures, usually in shades of grey. However, it is also possible to provide the data record in colour so as to better emphasis particular contrasts. By means of machine-based evaluation, the colours or shades of grey can be associated with absolute density values that are integrated in the representation. In this arrangement, density determination is advantageously implemented by means of an evaluation program, wherein absolute density values are also output to the viewer for orientation.

The following two variants of the invention are preferred. In the first case the bone-density equivalent material is directly integrated in the jig that formerly was present in the system. This approach is associated with an advantage in that no additional fixture for the phantom is required. Furthermore, in this case the phantom is held between the teeth in the body of the patient and thus in particularly close proximity to the region of interest.

In the second case the phantom is brought with a separate fixture, from the outside, into the immediate vicinity of the jaw region of the patient. Positioning outside the patient is associated with an advantage in that it is not absolutely necessary to completely disinfect the calibration phantom in an expensive manner. The phantom can be held by means of a flexibly swivellable fixture or a fixture that is rigid for the purpose of patient fixing or patent positioning (e.g. a jig). In this arrangement, direct embedding of the bone-equivalent material in the device for positioning the patient, for example in a chin support, can also be advantageous. Precise and reproducible positioning of the phantom obviates the need to use search-and segmenting algorithms to extract the bone-density voxel values, because the bone-equivalent material is located at a known position in the image volume. Positioning the fixture of the phantom outside the patient also ensures greater variability in positioning.

Irrespective of this first core idea, a further idea consists of inserting the calibration phantom during imaging in a body cavity of the patient, in particular in the oral cavity, so that the image data and the calibration data can be photographed in the framework of the same shot, without the need for further auxiliary means. In this position the phantom is optimally placed at the location of the action so that precise determination of tissue densities is possible.

Figure 2:
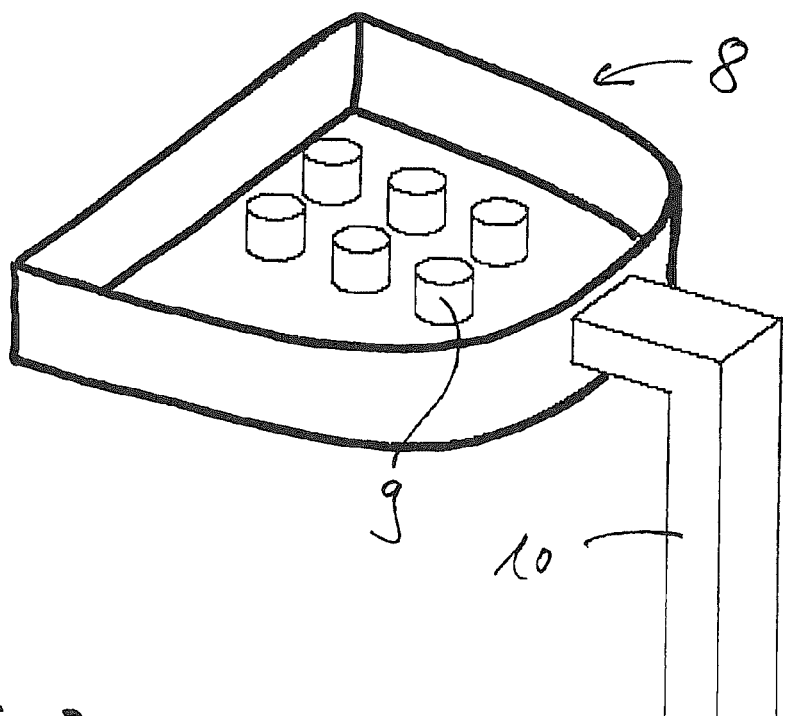

Below, the invention is explained in more detail with reference to FIGS. 1 to 3. The following are shown:

FIG. 1 a fixed patient with a calibration phantom for an external fixture;

FIG. 2 a calibration phantom integrated in a jig; and

Figure 3:
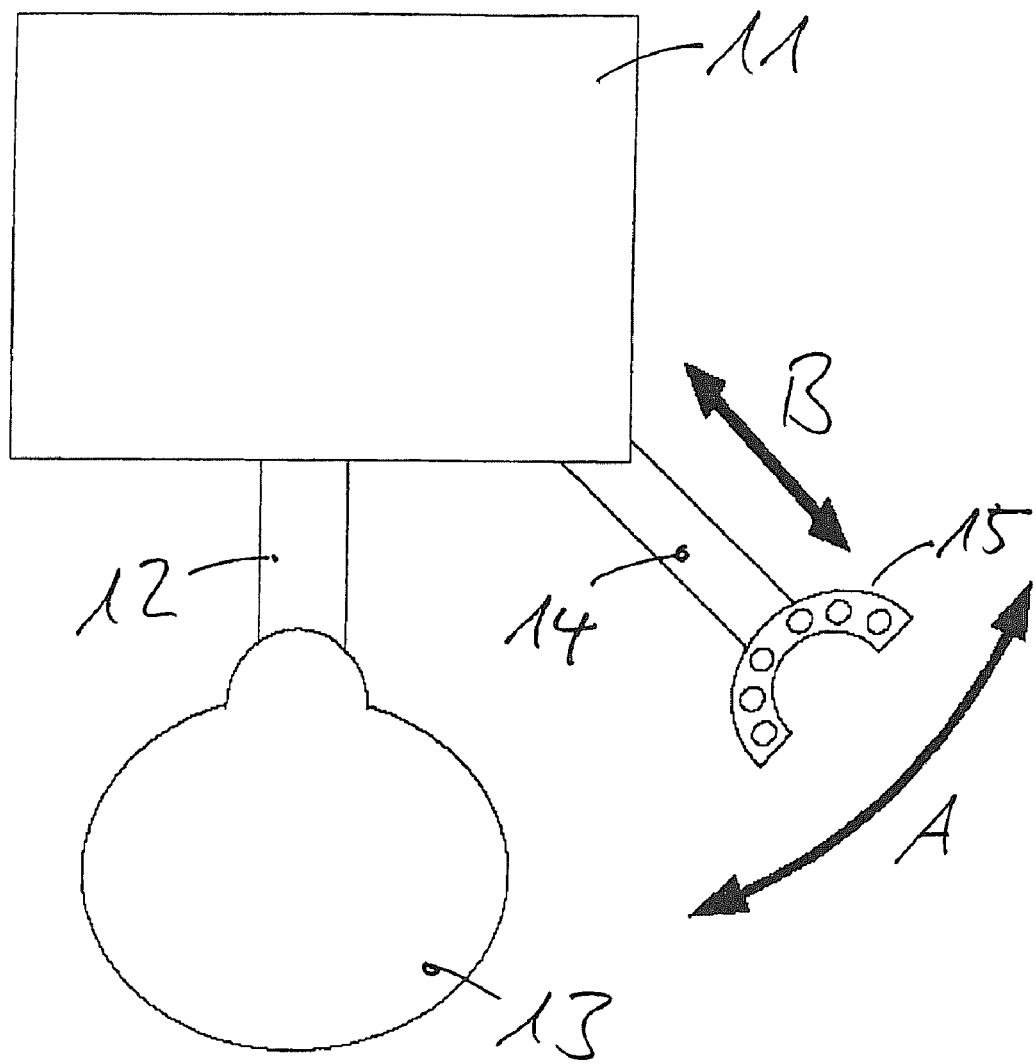

FIG. 3 a system with a variable fixture.

FIG. 1 diagrammatically shows the head, especially the jaw region 1, of a patient who has been prepared for taking an image sequence with a cone beam scanner. The teeth 2 of the patient are biting a jig of a matrix that matches the dentition geometry, so as to ensure that the head is fixed while the image sequence is taken. Correspondingly the jig is held on a stand 4 by way of a support 3, wherein the stand 4 is immobile. Furthermore, a calibration phantom 5 that is bent in a U-shape, is also attached to the stand, which calibration phantom 5 is held underneath the jig. The calibration phantom 5 comprises a casing 6 made of soft plastic, which casing 6 is in particular flexible, that is transparent to X-ray radiation. The casing 6 comprises individual cylinders 7 of a bone-equivalent material, for example of hydroxyapatite, which cylinders 7 comprise different but defined densities. With reference to the image data of these cylinders 7, calibration of the tissue density can take place later on. The calibration phantom 5, which is held on the stand 4, is height-adjustable, and its flexible casing 6 can adapt to the contour of the patient. An inflexible design of this arrangement can be advantageous if the precise position of the phantom in the image volume needs to be known.

FIG. 2 shows a jig 8, in which the cylinders 9 comprising the bone-equivalent material are directly integrated. For fixation, the patient's mouth encloses this jig 8 which is attached to a stand by way of a fixture 10. In each image, this integrated jig is available for evaluation, without this requiring any additional expenditure. Single-use jigs can comprise recesses into which the bone-equivalent material is placed prior to a scan, after which said bone-equivalent material can be removed. The "fixture" is disposable.

With this variant of the phantom, in which the bone material elements are arranged in the centre of the jig, interfering influences can be further minimised by metal artefacts.

FIG. 3 shows parts of an imaging system in which a fixture 12 for a conventional jig is affixed to a column 11. The column forms part of a system that comprises an X-ray source that can be moved around the skull of a patient who is sitting or standing; a detector device for taking up the X-ray radiation that has been weakened by the skull, in particular by the jaw; and a device, in particular a jig, for fixing the skull in the system. In this case the jig contained in the mouth of the patient 13 is not visible. Furthermore, a movable fixture 14 has been affixed to the column, which fixture 14 holds a calibration phantom 15 analogous to that in FIG. 1. By way of the fixture 14, the phantom 15 can be swivelled (arrow A) and axially displaced (arrow B). Vertical mobility is also provided. The stand can thus be moved in several degrees of freedom and can be affixed in a set position. By way of such a stand, which is designed as a positionable extension arm, the bone-equivalent material can be positioned near the jaw. The corresponding phantom can be removable, should it not be required.

The invention claimed is:

1. A method for pictorially representing and determining tissue densities of a body region of a patient, wherein a set of three-dimensional image data representing the body region as well as calibration data that is provided as three-dimensional image data and represents a calibration phantom having a previously known density are photographed by generating an image while the tissue densities are derived from a comparison of the calibration data with the image data, comprising photographing the image data and the calibration data in a framework of a same shot and in an upright position of the patient; and holding the calibration phantom in an immediate vicinity of the body region that is to be photographed during the shot by a fixture, which calibration phantom is fixed independently of the patient's body and in a defined relation to an imaging device.

2. The method according to claim 1, wherein the patient is positioned in a defined relation to the calibration phantom.

3. The method according to claim 1, wherein from a comparison of the calibration data with the image data the spatial distribution of absolute density values is inferred.

4. The method according to claim 3, wherein the comparison is made automatically with an evaluation program, wherein absolute density values are output.

5. The method according to claim 1, wherein the image data and the calibration data are acquired by a scanner with the use of the cone-beam technology.

6. The method according to any claim 1, wherein the calibration phantom, which is held by the fixture, is arranged in the body in a reproducible position.

7. The method according to claim 1, wherein the body region is in the mouth, jaw or face region.

8. The method according to claim 1, wherein the upright position of the patient is sitting or standing.

9. The method according to any claim 1, wherein the calibration phantom, which is held by the fixture, is arranged in the oral cavity of the patient in a reproducible position.

10. A system for implementing the method according to claim 1, comprising:

an X-ray source that can be moved around the skull of a patient who is sitting or standing;

a detector device for taking up the X-ray radiation that has been weakened by the skull; and a device for fixing the skull in the system, comprising a calibration phantom, which is for positioning in the immediate vicinity of the skull, and which is held on a fixture, which calibration phantom is fixed in a defined relation to the imaging device.

11. The system according to claim 10, wherein the calibration phantom forms part of a device for fixing or positioning the patient.

12. The system according to claim 10, wherein the fixture can be moved in several degrees of freedom and can be locked in a set position.

13. The system according to claim 10, wherein the calibration phantom is integrated in the device for fixing the skull in the system.

14. The system according to claim 13, wherein in the device for fixing the skull in the system, one or several recesses are provided which can be removably inserted in formed bodies made of bone-equivalent material.

15. The system according to claim 10, wherein the X-ray radiation has been weakened by the jaw.

16. The system according to claim 10, wherein the a device for fixing the skull in the system is a jig.

17. The system according to claim 10, wherein the calibration phantom forms part of a chin support for fixing or positioning the patient.

18. The system according to claim 10, wherein the calibration phantom is integrated in the device for fixing the skull in the system, which is a jig.

19. The system according to claim 10, wherein in the device for fixing the skull in the system, which is a jig, one or several recesses are provided which can be removably inserted in formed bodies made of bone-equivalent material.

20. The system according to claim 13, wherein the bone-equivalent material is hydroxyapatite.

* * * * *